United States Patent [19]
Gavin et al.

[11] Patent Number: 6,074,609
[45] Date of Patent: Jun. 13, 2000

[54] SYSTEMS FOR ARRAYING BEADS

[75] Inventors: Robert M. Gavin, San Jose; Jeffrey H. Sugarman, Los Altos; Haim Kedar, Palo Alto; Sam Chan, San Jose, all of Calif.

[73] Assignee: Glaxo Wellcome Inc., Research Triangle Park, N.C.

[21] Appl. No.: 08/834,803

[22] Filed: Apr. 3, 1997

Related U.S. Application Data

[63] Continuation-in-part of application No. 08/637,123, Apr. 24, 1996, abandoned.

[51] Int. Cl.[7] .................................................. G01N 33/551
[52] U.S. Cl. .............................. 422/99; 422/69; 422/100; 422/101; 435/287.3; 435/294.1; 436/178; 436/524; 436/526
[58] Field of Search ................................ 422/69, 99, 100, 422/101; 435/287.3, 294.1; 436/524–534, 178

[56] References Cited

U.S. PATENT DOCUMENTS

| | | |
|---|---|---|
| 3,568,735 | 3/1971 | Lancaster . |
| 3,598,251 | 8/1971 | Sieurin . |
| 3,932,141 | 1/1976 | Beall et al. . |
| 3,940,172 | 2/1976 | Hutson et al. . |
| 4,101,284 | 7/1978 | Difiglio et al. . |
| 4,266,905 | 5/1981 | Birk et al. . |
| 4,649,116 | 3/1987 | Daty et al. . |
| 4,768,919 | 9/1988 | Borgman et al. . |
| 4,770,454 | 9/1988 | Muscher et al. . |
| 4,837,159 | 6/1989 | Yamada . |
| 4,858,975 | 8/1989 | Ogawa . |
| 4,887,351 | 12/1989 | Porterfield et al. . |
| 4,894,343 | 1/1990 | Tanaka et al. . |
| 4,937,048 | 6/1990 | Sakai et al. . |
| 4,981,315 | 1/1991 | Poli et aL. . |
| 5,171,537 | 12/1992 | Wainwright et al. . |
| 5,185,269 | 2/1993 | Wells . |
| 5,207,467 | 5/1993 | Smith . |
| 5,280,979 | 1/1994 | Poli et al. . |
| 5,382,512 | 1/1995 | Smethers et al. . |
| 5,414,955 | 5/1995 | Morin . |
| 5,474,744 | 12/1995 | Lerch . |
| 5,567,326 | 10/1996 | Ekenberg et al. . |
| 5,702,950 | 12/1997 | Tajima . |
| 5,935,859 | 8/1999 | Elliot et al. . |

FOREIGN PATENT DOCUMENTS

| | | |
|---|---|---|
| 43 29 791 | 3/1995 | Germany . |

OTHER PUBLICATIONS

Fischer Scientific Catalog 1988, pp. 884–885, 890, 1988.

Normie (Sep./Nov. 1996), article "System uses photonics for early tumor detection," in Biophotonics News, Biophotonics International, pp. 24–25.

Kenichi et al. (1989), "Method for moving spherical carrier for antigen–antibody reaction," Patent Abstracts of Japan, vol. 13, No. 306 (P–897).

*Primary Examiner*—Jan Ludlow
*Attorney, Agent, or Firm*—Darin J. Gibby; Lauren L. Stevens

[57] ABSTRACT

The invention provides systems and methods for processing a plurality of solid supports which preferably have chemical compounds synthesized thereon. According to one exemplary method, the solid supports (12) are held in a common storage location (10). At least some of the solid supports (24) are attracted from the storage location to selected areas within a defined receiving region (20) so that the solid supports which are attracted to the selected areas within the receiving region are separated and spaced apart from each other.

6 Claims, 13 Drawing Sheets

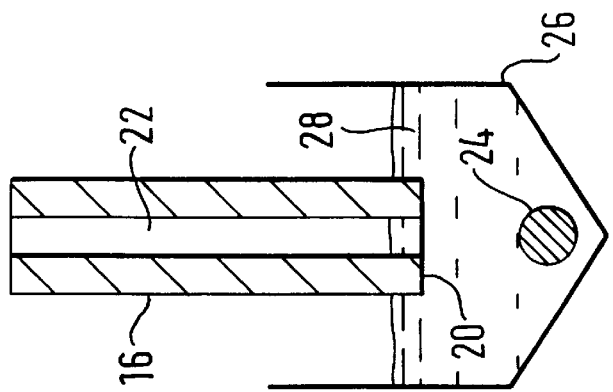
FIG. 4
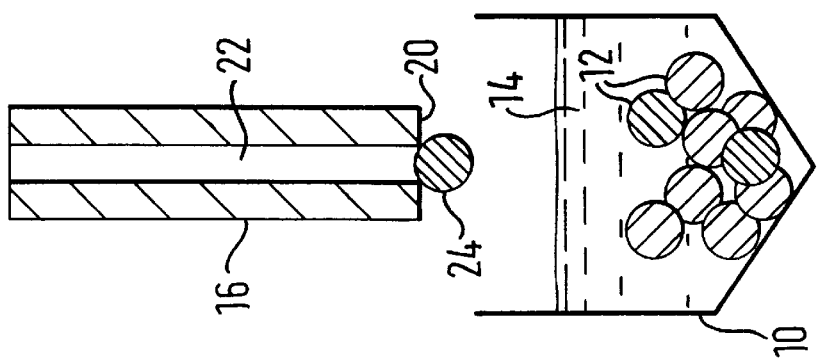
FIG. 3
FIG. 2
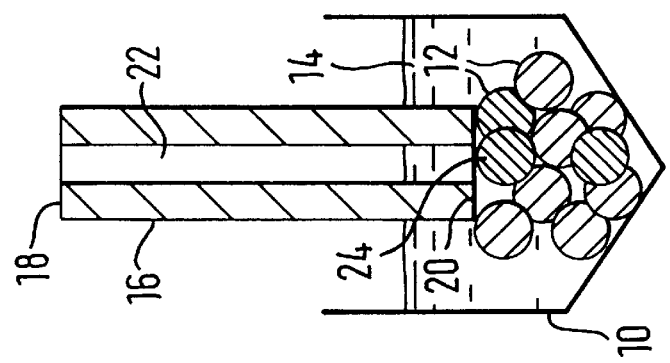
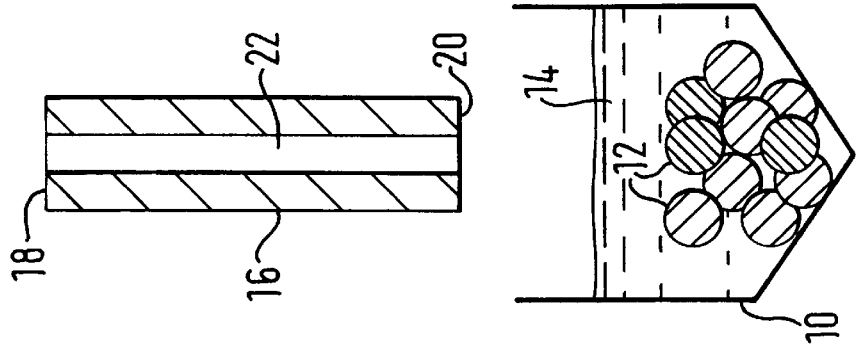
FIG. 1

SYSTEMS FOR ARRAYING BEADS

CROSS REFERENCE TO RELATED APPLICATIONS

This application is a continuation-in-part application of U.S. application Ser. No. 08/637,123, filed Apr. 24, 1996, now abandoned the complete disclosure of which is herein incorporated by reference.

BACKGROUND OF THE INVENTION

This invention relates generally to the field of chemical evaluation, particularly with chemical compounds which have been synthesized onto solid supports such as beads. More particularly, the invention relates to the organization of the solid supports following synthesis and the performance of assays on the chemical compounds in order to evaluate and/or identify particular compounds which are of interest.

In modern chemistry large libraries of chemical compounds are often created from which certain compounds which are of interest may be identified. The creation of such libraries may be accomplished with a synthesizing process where various compounds are placed on solid supports. Such processes are described in, for example, U.S. Pat. No. 5,503,805 and U.S. patent application Ser. No. 08/146,886, filed Nov. 2, 1993, now U.S. Pat. No. 5,639,603, both herein incorporated by reference.

The synthesis of compounds onto solid supports is advantageous in that the solid supports serve as a transport device to facilitate movement of the compounds. The solid supports also allow different compounds to be separated from other compounds in a complex mixture and allow for the release of the compound on demand.

In order to evaluate specific compounds, at least some of the compounds are released from the solid supports and assays are performed. The assay results are then measured and certain solid supports may be chosen for decoding or other processes, such as deconvolution and LCMS.

Although synthesizing processes and the performance of assays are known in the art, there are a number of problems that have yet to be addressed relating to the organization of the solid supports following synthesis so that the compounds can be evaluated. For example, the solid supports need to be separated from each other, preferably in some organized manner, so that the compounds can be released and assays performed.

The separation and organization of the solid supports is rendered especially difficult due to their size and construction. For instance, the solid supports are usually on the order of about 5 $\mu$m to 300 $\mu$m, making their handling difficult. Further, it is usually desirable to process the solid supports within a liquid medium, such as water or solvent, to prevent (among other reasons) the solid supports from sticking together. Hence, separating the solid supports from each other while within the liquid to perform assays can be difficult and challenging. The time, labor and materials required to process the solid supports and evaluate the compounds can also be significant. This is of particular concern as it becomes more desirable to create larger libraries.

It would therefore be desirable to provide systems and methods for processing solid supports following synthesis so that particular compounds may be evaluated. It would be especially desirable if such systems and methods facilitated the organization and separation of the solid supports so that compounds may easily be released and assays performed. In this manner, it is anticipated that the time, labor and materials required to evaluate compounds within large libraries may be greatly reduced.

SUMMARY OF THE INVENTION

The invention provides systems and methods for processing a plurality of solid supports which preferably have chemical compounds synthesized thereon. According to one exemplary method, the solid supports are held in a common storage location. At least some of the solid supports are attracted from the storage location to selected areas within a defined receiving region so that the solid supports which are attracted to the selected areas within the receiving region are separated and spaced-apart from each other. In this manner, the solid supports are arranged such that further evaluation of the compounds that are synthesized on the solid supports is facilitated. For example, when the solid supports are placed at the selected areas, at least some of the compounds may be released and assays performed on the released compounds in order to further evaluate the compounds.

The selected areas are preferably arranged in an organized pattern, such as a two-dimensional array. Such organization of the selected areas further facilitates evaluation of the compounds. In one aspect of the method, only one solid support is attracted to each of the selected areas. In another aspect of the method, the compounds may be released and the assays performed either while the solid supports remain attached to the selected areas or after the solid supports have been released.

In one exemplary aspect, the attracting step comprises introducing a transfer member defining at least one lumen with an open distal end into the common storage location. Suction is applied to the lumen to draw one of the solid supports against the distal end. In one preferable aspect, the transfer member comprises a plate having a plurality of lumens. With this arrangement, the plate may then be introduced into the storage location to draw multiple solid supports against the plate. Assays may then be performed on compounds in a variety of ways. For example, the assays may be performed while the solid supports remain attached to the plate. Alternatively, assays may be performed after transferring the solid supports to another location. One particular advantage of the plate is that it is disposable and may be discarded after use, thereby eliminating the need to clean the plate after each use.

In another exemplary aspect, the common storage location includes a liquid medium. With this arrangement, the attracting step in one embodiment comprises swirling the liquid medium within the storage location and introducing at least one tube having a hole therein into the liquid medium to capture the swirling solid supports. The hole is preferably included on a side of the tube and suction is provided to the tube to assist in drawing the solid supports into the hole. After a solid support is captured, pressure may be applied to the tube to expel the solid support from the tube, preferably at a distal end of the tube.

In still a further aspect, the attracting step comprises providing a magnetic material on the solid supports and attracting the solid supports to the selected areas with a magnet. For instance, the defined receiving region may comprise a plate having a plurality of wells, with each well including a magnet. In this manner, the solid supports are drawn by the magnets into the wells.

Alternatively, each selected area of the receiving region may be chemically treated so that the solid supports may be covalently attached to selected areas. In a further alternative, the solid supports may be electrostatically attracted to the selected areas.

In still a further aspect, the receiving region comprises a plate having a planar surface. The selected areas comprise wells formed within the plate, and the attracting step comprises pouring the solid supports onto the planar surface. An edge is then moved across the surface to place the solid supports into the wells. Preferably, the solid supports will be suspended within a suspension medium, such as a gel which is poured onto the plate.

In yet another aspect, the solid supports are suspended within a suspension medium, and the attracting step comprises placing the medium onto a mesh material. The medium is then manipulated to organize or array the solid supports on the mesh. The solid supports may then be contacted with a plate having a gel to transfer the solid supports from the mesh to the plate.

In still yet another aspect, the solid supports are held within a liquid medium, and the attracting step comprises passing the liquid medium through a central channel within a housing. As the solid supports pass through the channel, they are drawn into and captured within vented nodes which extend from the central channel. To assist in drawing the solid supports into the nodes, suction may be applied to each of the nodes.

The invention further provides an exemplary system for processing a plurality of solid supports. The system is configured to facilitate the evaluation of chemical compounds which have been synthesized onto the solid supports. The system comprises a receiving region comprising a plurality of spaced apart selected areas such that at least some of the solid supports may be transferred from a common storage location by attraction to selected areas of the receiving region by the action of an attracting force. The selected areas are arranged such that the attracted solid supports are separated and spaced apart from each other when attracted to the receiving region.

The selected areas are preferably arranged in an organized pattern, such as a two-dimensional array. The system may also include a chemical synthesizer for synthesizing chemicals onto the solid supports prior to storing the solid supports in the storage location.

In one exemplary aspect, the system comprises a plate having a plurality of holes and a vacuum source. The plate is preferably disposable so that following processing of the solid supports the plate can be discarded. In this manner, the plate need not be cleaned after each use. Another advantage of the plate is that assays may be performed while the solid supports remain attached to the plate. For example, the plate may be pressed against a surface having a reactive substance thereon to introduce the chemicals on the solid supports to the reactive substance. As another example, a housing defining a plurality of wells may be placed onto the plate, with the wells being received over the solid supports. In this way, various reagents or other fluids may be placed into the wells to facilitate evaluation of the compounds.

In another exemplary aspect, the system comprises a plurality of capillary tubes and a vacuum source. With this arrangement, the capillary tubes may be placed into the storage location and a vacuum applied to draw the solid supports against the capillary tubes.

Typically, the common storage location includes a liquid medium. In still another exemplary aspect, the attracting force will comprise a means for swirling the liquid medium within the storage location such that when a tube having a hole therein is placed into the liquid medium, the solid supports are captured as they are circulated within the storage location.

In yet another exemplary aspect, the attracting force will comprise a magnetic force and thus, the receiving region will comprise a plate having a plurality of magnets at the selected areas. With this arrangement, the solid supports will include a magnetic material so that the solid supports may be attracted to the selected areas. Alternatively, the attracting force may comprise a chemical bond and the receiving region may comprise a plate which is chemically treated at the selected areas for covalently or non-covalently attracting the solid supports.

In still another aspect, the solid supports are suspended within a suspension medium, and the attracting force includes placing the medium onto a mesh material and manipulating the material to organize or array the solid supports on the mesh. The solid supports may then be contacted with a plate having a gel to transfer the solid supports from the mesh to the plate.

In still yet another exemplary aspect, the receiving region comprises a plate having a planar surface. A plurality of wells are included in the plate for receiving the solid supports. An edge is further provided which may be moved across the plate to move the solid supports into the wells, i.e., the attracting force.

In another alternative aspect, the receiving region comprises a housing defining a central channel and a plurality of vented nodes which extend from the central channel. In this manner, the solid supports may be passed through the central channel in the presence of a liquid medium. As the solid supports pass through the channel, they are drawn into the vented nodes. Preferably, the nodes will be sized to receive only a single solid support. A vacuum source may also be provided to assist in drawing the solid supports into the nodes.

BRIEF DESCRIPTION OF THE DRAWINGS

FIGS. 1–4 illustrate an exemplary method for transferring an article held within a liquid medium from one location to another according to the present invention.

DETAILED DESCRIPTION OF THE SPECIFIC EMBODIMENTS

Figure 5:
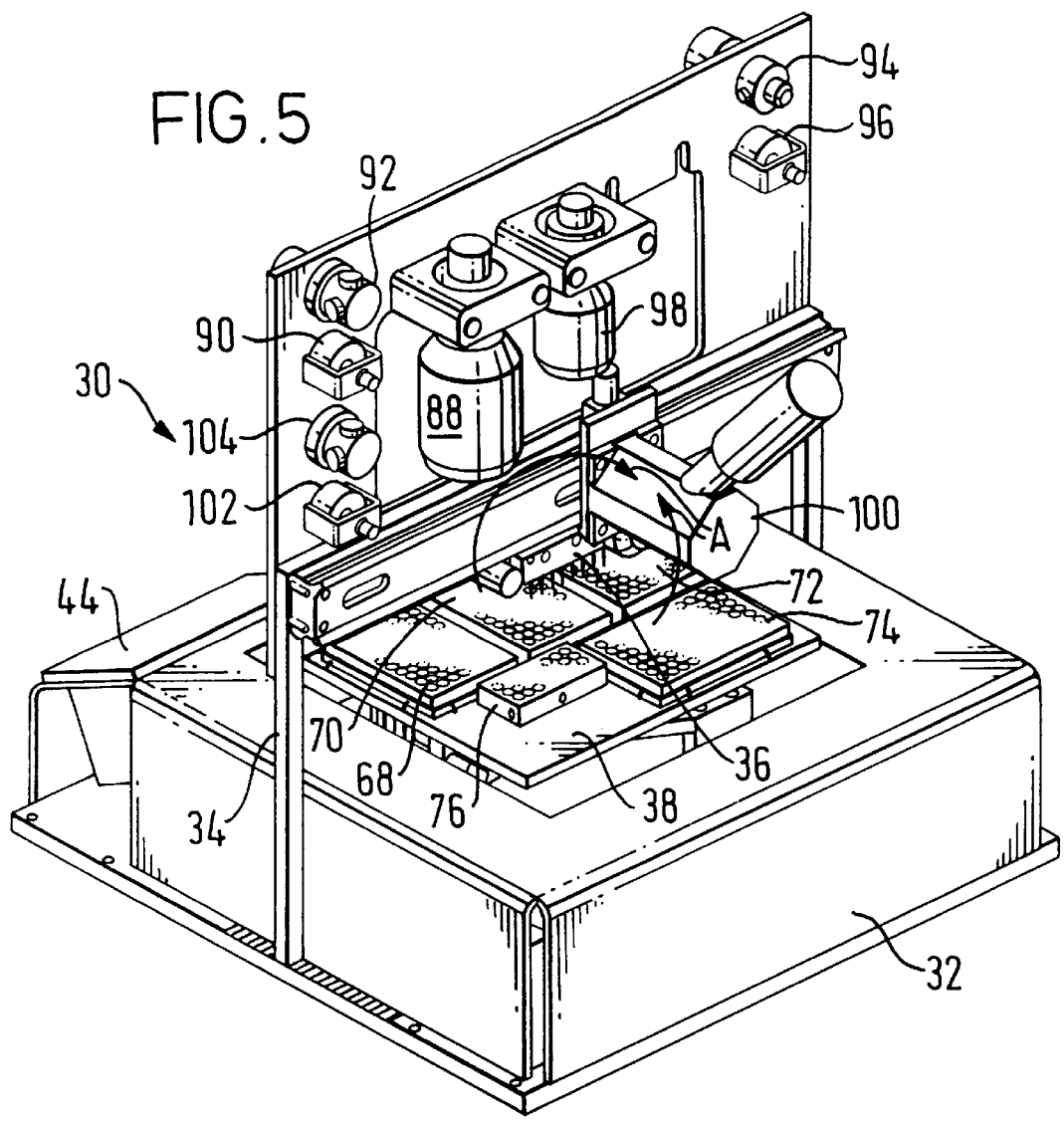
FIG. 5 is a perspective view of an exemplary system for transporting articles held within a liquid medium from one location to another according to the present invention.

The invention provides systems and methods for processing solid supports which have chemical compounds synthesized thereon. The solid supports that are of interest to the invention will be small, typically on the order of 5 $\mu$m to 300 $\mu$m in diameter, more usually from about 80 $\mu$m to 200 $\mu$m. The solid supports will usually comprise beads on which the compounds have been synthesized, such as by the processes described in U.S. Pat. No. 5,503,805 and U.S. patent application Ser. Nos. 08/146,886, filed Nov. 2, 1993, now U.S. Pat. No. 5,639,603 both previously incorporated by reference. The beads are usually constructed of a polymer such as polystyrene and polyethylene glycol and are generally spherical in geometry. Such beads are commercially available from, for example, Nova BioChem.

Following synthesis, the beads are usually placed into a common storage location or reservoir and stored in a random manner. The invention provides for the separation, and in some cases, the organization of the solid supports so that evaluation of the compounds may proceed. Once separated, at least some of the compounds are released from the solid supports and assays are performed on the released compounds. The assay results are then measured and certain solid supports may be chosen for decoding in order to identify or further evaluate the compounds.

To separate the solid supports from each other, at least some of the solid supports are attracted to selected areas within a receiving region so that each solid support is separated from each other. Usually, the selected areas will form an organized pattern, such as a two-dimensional array, to facilitate further processing.

Once attached to the receiving region, assays can be directly performed on the solid supports, or the solid supports can be released into wells or other holding vessels where assays are performed. The systems and methods of the invention are compatible with a variety of assay formats including "open well" formats, "closed well" formats and "open two-dimensional formats." In open well formats, the solid supports are transferred to open wells which are isolated from each other. Reagents and other liquids can be filled or drained from the open top of each well. In closed well formats, the solid supports are received into closed wells where the assay liquid in each well is isolated from the outside environment. In open two-dimensional formats, the solid supports may remain attached to the receiving region and placed onto a flat surface having a liquid or a gel thereon. The compounds then diffuse into the liquid or gel to facilitate their evaluation. Short and limited diffusion times facilitate this process. Further, with this format, the solid supports need not be organized into a pattern.

As illustrated in the attached drawings, various embodiments are provided for attracting the solid supports from a common source and to selected areas of a receiving region where the solid supports are separated from each other. Referring to FIGS. 1–4, one particular method for attracting and separating solid supports will be described. As shown in FIG. 1, a common storage location or reservoir 10 holds a plurality of solid supports 12 within a liquid medium 14. The common storage location 10 may be any container, for example, beakers, vials, and the like, having an opening of sufficient width to allow access of the transfer member. A transfer member 16 having a proximal end 18 and distal end 20 is positioned vertically above reservoir 10. A lumen 22 extends between proximal end 18 and distal end 20 of transfer member 16. Lumen 22 has a cross-sectional area which is smaller than the size of solid supports 12. Usually, the cross-sectional area will be circular and of a size such that the lumen diameter is smaller than the size of the solid support. In an exemplary embodiment, the lumen 22, or more specifically, the distal end 20 of the lumen 22, will serve as the selected area of the receiving region with the transfer member comprising the receiving region.

To remove a single solid support from the plurality of solid supports 12, distal end 20 is lowered into liquid medium 14 until in the vicinity of solid supports 12 as shown in FIG. 2. An attracting force, preferably a vacuum from a vacuum source (not shown), is created within or applied to lumen 22 to draw one of the solid supports 24 from the group of solid supports 12 onto the distal end 20 of lumen 22 (i.e., a selected area of the receiving region). Transfer member 16 is then slowly lifted from reservoir 10 to remove the single solid support 24 from reservoir 10. Since the size of lumen 22 is smaller than the size of solid support 24, the vacuum will hold solid support 24 at distal end 20.

According to some embodiments, it will not be necessary to continuously apply the attracting force to ensure that the solid support is attracted to the selected area of the receiving region. For example, other retaining forces that may be distinct from the attracting force may cause the solid support to be retained. Examples of retaining forces will be appreciated by those of skill in the art and include, but are not limited to, electrostatic attraction, physical entrapment, vacuum, covalent or noncovalent bonding, magnetic attraction, and the like.

Transfer member 16 is lifted from reservoir 10 and through the liquid/air interface at a rate of speed which is slow enough so that surface tension forces from liquid medium 14 will help to strip off any solid supports 12 which are stuck or attached to solid support 24. Although the rate of speed at which transfer member 16 is lifted from reservoir 10 is based on a variety of factors, including the strength of the retaining force, e.g., the amount of vacuum within lumen 22, the type of liquid medium 14, and the size of solid support 24 relative to the size of lumen 22, a preferred rate of speed will be in the range from about 0.075 cm per second to about 1.5 cm per second, more preferably from about 0.075 cm per second to about 0.5 cm per second.

After solid support 24 has been removed from reservoir 10, transfer member 16 is positioned in a test well 26 as shown in FIG. 4. Test well 26 holds a liquid medium 28 which will receive the solid support 24. In one embodiment, solid support 24 is released from the transfer member by ceasing the application of the vacuum (or other retaining force) while solid support 24 is within liquid medium 28. Optionally, a fluid may be forced through lumen 22 to assist in separating solid support 24 from transfer member 16. When solid support 24 is being drawn against distal end 20, lumen 22 will often at least partially fill with some of liquid medium 14. Hence, when the fluid is forced through lumen 22, an amount of liquid medium 14 will also be expelled into test well 26. An exemplary fluid which may be forced through lumen 22 to expel solid support 24 comprises nitrogen. The nitrogen will preferably be forced through lumen 22 both while solid support 24 is being expelled and while transfer member 16 is raised from the liquid medium 14. One of skill in the art will readily appreciate that other ejecting forces, such as shaking, demagnetization, heating, and the like may be used to initiate the release of the solid support from the selected area of the receiving region.

After solid support 24 has been placed into test well 26, transfer member 16 may be repositioned over reservoir 10 (or another reservoir having solid supports) to draw another of the solid supports 12 to distal end 20. Transfer member 16 may be then positioned over another test well (or over test well 26) to place the attached solid support therein.

It will be appreciated that more than one bead may be removed from a well. This may be accomplished by simultaneously placing more than one transfer member into a well or by repeating the process of placing a transfer member in a well and removing a bead therefrom.

Referring now to FIG. 5, an exemplary system 30 for transporting solid supports will be described. System 30 includes a base portion 32 and a bridge 34. Bridge 34 holds a capillary manifold 36 over a platform member 38. In this manner, a variety of bead reservoirs and target wells may be placed on platform member 38 so that beads may be transferred therebetween with capillary manifold 36 as described in greater detail hereinafter.

Figure 6:
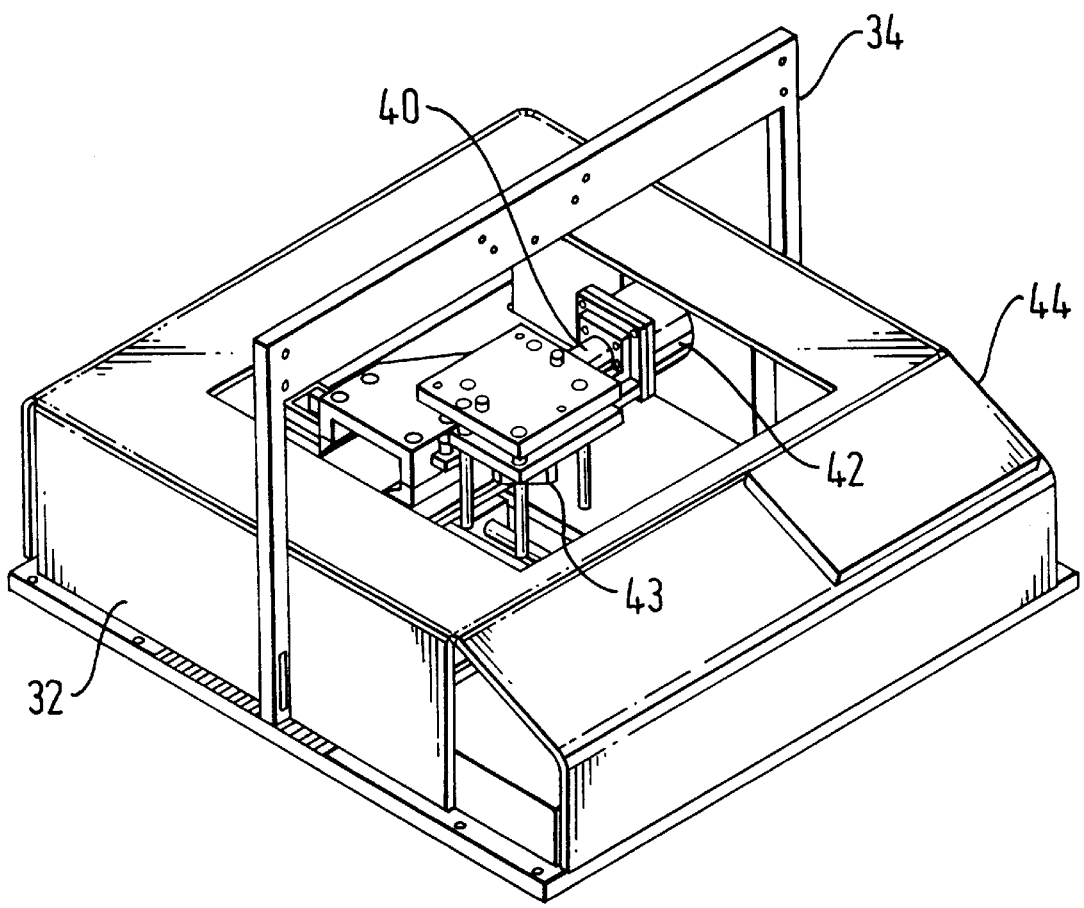
FIG. 6 is a perspective view of a base portion of the system of FIG. 5 having a movable mounting plate.

Referring to FIG. 6, construction of base portion 32 and bridge 34 will be described in greater detail. Base portion 32 includes a mounting plate 40 onto which platform member 38 (see FIG. 5) is attached. Mounting plate 40 has three degrees of freedom so that it may be moved both horizontally (in two dimensions) and vertically. Mounting plate 40 is translated horizontally by a motor 42 and vertically by a separate motor 43. Motor 42 is in turn controlled by a controller (not shown) held within base portion 32 and is operated using an operator interface 44. Bridge 34 is securely attached to base portion 32 so that objects held by bridge 34 will be stationary relative to base portion 32. In this manner, mounting plate 40 may be positioned at a wide variety of locations relative to an object held on bridge 34.

Figure 7:
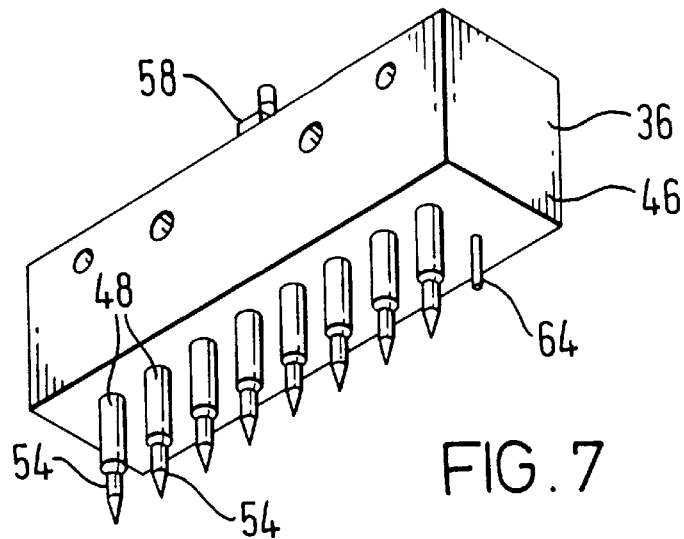
FIG. 7 is a perspective view of a capillary manifold of the system of FIG. 5.
Figure 8:
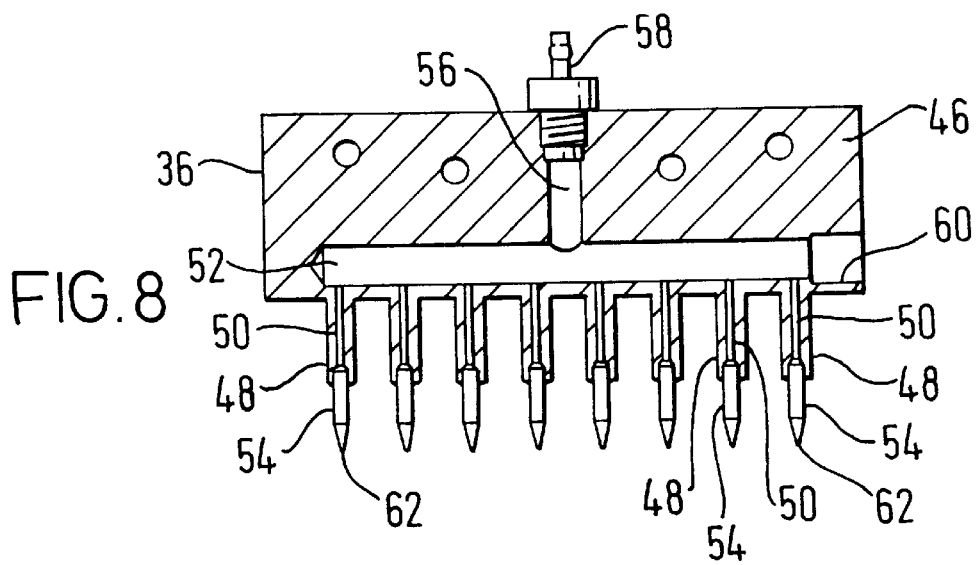
FIG. 8 is a cross-sectional side view of the manifold of FIG. 7.
Figure 9:
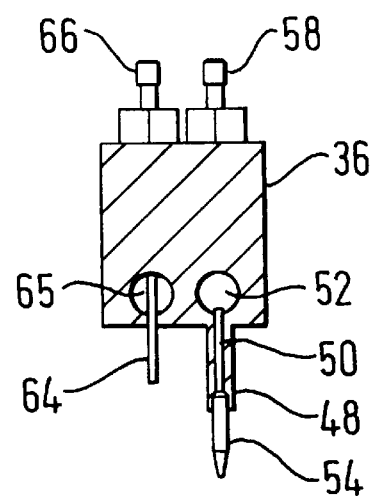
FIG. 9 is a cross-sectional end view of the manifold of FIG. 7.

Referring now to FIGS. 7–9, construction of capillary manifold 36 will be described in greater detail. Capillary manifold 36 includes a housing 46 having a plurality of finger-like projections 48. The finger-like projections 48 may be constructed to be shorter than shown or may be excluded altogether. In this embodiment, finger-like projections 48 assist in allowing deep penetration into the wells. As best shown in FIG. 8, projections 48 each have a central lumen 50 extending therethrough. A common lumen 52 in housing 56 is in communication with each of central lumens 50. Pressed into the opposite ends of lumens 50 are capillary tubes 54. A vacuum/pressure line 56 is in communication common lumen 52 so that a vacuum or positive pressure may be selectively provided in capillary tubes 54. A connector 58 is inserted into line 56 so that suitable tubing may be connected to line 56. Common lumen 52 includes an open end 60 which is plugged during operation. Open end 60 is fashioned in this manner for manufacturing convenience.

Each capillary tube 54 has an open distal end 62 against which individual beads may be drawn (i.e., the selected area of the receiving region). The opening in distal end 62 is preferably smaller in size than the size of the beads so that beads will be prevented from passing through the capillary tubes. The opening in distal end 62 is also configured to be large enough so that sufficient suction may be provided to hold a bead against distal end 62. For example, in the case where the beads have a mean size in the range from about 100 $\mu$m to about 200 $\mu$m, distal end 62 will preferably have an opening with a size in the range from about 40 $\mu$m to about 80 $\mu$m.

Housing 46 will preferably be constructed of any material which is chemically compatible with the fluids being used, and capillary tubes 54 will be preferably constructed of ceramic. Suitable capillary tubes 54 are commercially available from suppliers such as Kulicke and Soffa.

As best shown in FIGS. 7 and 9, capillary manifold 36 may optionally include a plurality of target fluid delivery lines 64 which are spaced apart from each of the capillary tubes 54. Target fluid delivery lines 64 may be employed to fill target wells with a fluid prior to receiving beads. Optionally, target fluid delivery lines 64 may also be employed to replenish fluid removed from the source wells during dispensing. The target fluid is delivered to delivery lines 64 through a connector 66 (see FIG. 9) where it passes through a pressure line (not shown) and a common lumen (not shown) similar to line 56 and common lumen 52 as previously described. In this manner, a target fluid may be delivered to test wells by positioning delivery lines 64 above the test wells and supplying a target fluid through connector 66.

Referring back to FIG. 5, the items held on platform member 38 will be described. Platform member 38 includes wells or reservoirs having libraries of beads which are to be transferred to other individual wells or reservoirs, which are also held on platform member 38. As previously described, platform member 38 may be appropriately positioned so that capillary manifold 36 may be aligned with the appropriate wells or reservoirs. The particular location of the wells or reservoirs having libraries of beads to be distributed or which are intended to receive single bead distributions may vary depending on the particular application. One workable configuration, which is not meant to be limiting, is illustrated in FIG. 5 where three single bead target plates 68, 70, 72 are arranged on one side of platform member 38. A bead reservoir plate 74 is included at one corner of platform member 38, and a miscellaneous plate is provided adjacent bead reservoir plate 74 and bead target plates 68 and 70.

Figure 10:
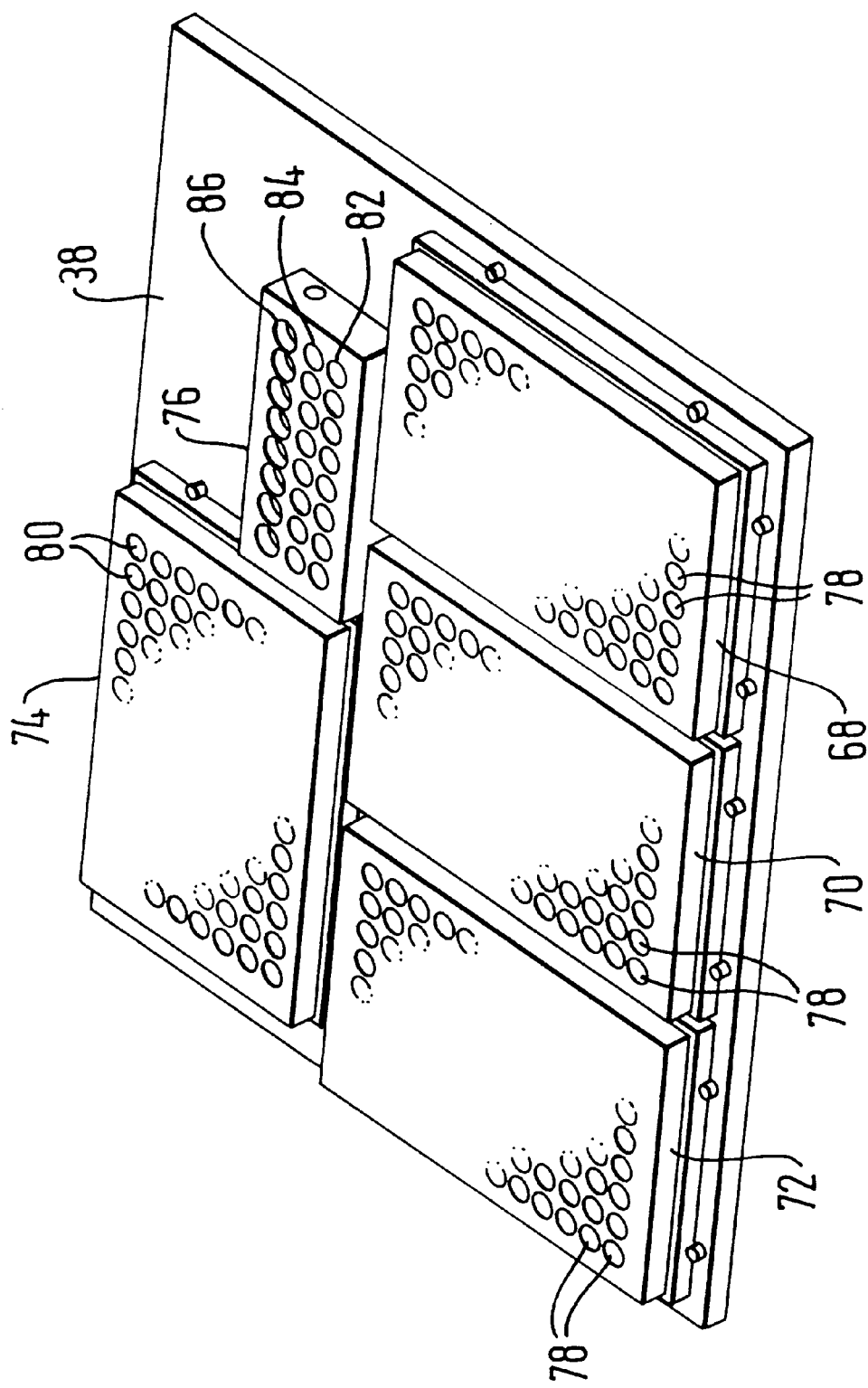
FIG. 10 is a perspective view of a platform member of the system of FIG. 5 having a variety of bead distribution plates and bead target plates.

Referring to FIG. 10, use of plates 68, 70, 72, 74 and 76 will be described in greater detail. Single bead target plates 68, 70, 72 each include a plurality of test wells 78 which are arranged in rows and columns. Test wells 78 are provided to receive a single bead after its transfer from a library. Bead reservoir plate 74 includes a plurality of holding wells 80 for holding pools or libraries of beads which are to be redistributed to test wells 78 of bead target plates 68, 70, 72. Miscellaneous plate 76 includes a row of reservoir wells 82 which may also be used to hold libraries of beads which are to be redistributed to wells 78 of bead target plates 68, 70, 72. In this manner, pools of beads may initially be stored in either reservoir wells 82 or holding wells 80, or both.

Miscellaneous plate 76 further includes a row of wash wells which each hold a solution suitable for washing capillary tubes 54 after beads have been transferred into test wells 78. An exemplary washing solution includes methanol. A row of priming wells 86 is further included in miscellaneous plate 76 and are used to prime target fluid delivery lines 64 before the target fluid is placed into test wells 78. To prime target fluid delivery lines 64, the lines are placed above priming wells 86 and the target fluid is delivered through lines 64 until any air or other gases are removed from lines 64.

Referring back to FIG. 5, operation of system 30 to transfer beads will be described. Initially, pools of beads are placed in holding wells 80 of bead reservoir plate 74 or reservoir wells 82 of miscellaneous plate 76. The pools of beads may be placed in wells 80 or 82 while plates 74 or 76 are on platform member 38. Alternatively, plates 74 and 76 may be removed from platform member 38 for convenient filling. The pools of beads will be held within a liquid having sufficient surface tension properties to cause any beads which are stuck to the bead of interest to be stripped off as the capillary tubes 54 are slowly removed from fluid. An exemplary liquid comprises water.

One or more of bead target plates 68, 70 or 72 is then placed on platform member 38 at an appropriate location. Before solid supports are placed in test wells 78 of plates 68, 70, or 72, it is desirable to have test wells 78 filled with a target fluid which is compatible with the beads. To enable test wells 78 to be filled with the target fluid, a target fluid supply 88 is attached to bridge 34. Target fluid supply 88 is in fluid communication with connector 66 (see FIG. 9) of capillary manifold 36 via tubing (not shown). A target fluid supply pressure gauge 90 and a target fluid supply regulator 92 are provided for monitoring and controlling the delivery of fluid from supply 88 to manifold 36.

Before the target fluid is delivered to test wells 78, target fluid delivery lines 64 will preferably be primed to remove any air or gasses from lines 64. Priming occurs by positioning priming wells 86 of miscellaneous plate 76 underneath fluid delivery lines 64. Movement of miscellaneous plate 76 is controlled at operator interface 44 which controls movement of platform member 38. With lines 64 positioned above wells 86, the target fluid from supply 88 is supplied for a time sufficient to ensure that the lines are primed.

Platform member 38 is then moved to align a first row of test wells 78 with fluid delivery lines 64. Target fluid from supply 88 is then delivered through fluid delivery lines 64 to place an appropriate amount of the target fluid within test wells 78. Platform member 38 is then lowered and moved to align a second row of test wells 78 with fluid delivery lines 64. This process is then repeated until all desired rows of test wells 78 are filled with the target fluid.

With test wells 78 filled with the target fluid, the pools of beads in wells 80 or 82 are ready to be redistributed to test wells 78. To redistribute the pools of beads, platform member 38 is moved to align capillary tubes 54 with a row of holding wells 80 or reservoir wells 82. Platform member 38 is then raised to place capillary tubes 54 within wells 80 or 82 and into the liquid medium. A vacuum is created within capillary tubes 54 to attract a single bead to each capillary tube 54. To create the vacuum, a vacuum source (not shown) is in communication with connector 58 (see FIG. 9) by appropriate tubing (not shown). A vacuum gauge regulator 94 and vacuum gauge 96 are provided for regulating and monitoring the amount of vacuum. A vacuum trap 98 is provided to prevent any liquid from being drawn into the vacuum source.

Figure 5A:
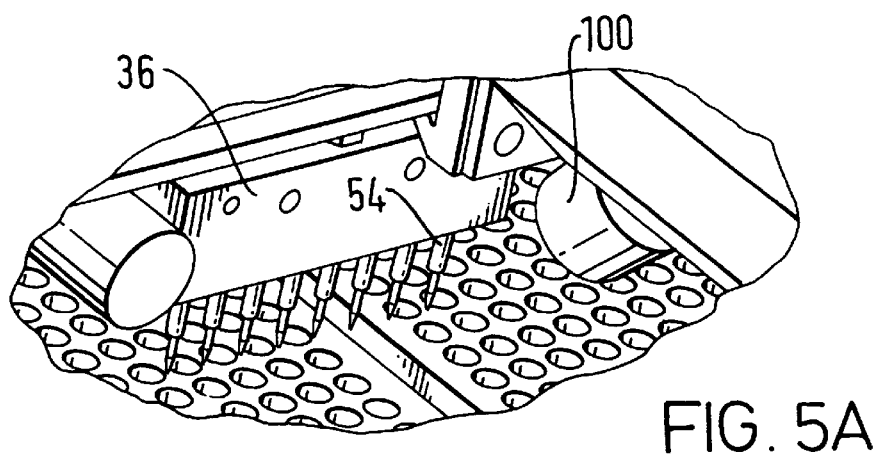
FIG. 5A is a more detailed view of the system of FIG. 5 taken along lines A—A.

After a bead has been attracted to each of the capillary tubes 54, platform member 38 is slowly lowered so that surface tension forces will assist in stripping any extra beads which may be stuck to the engaged bead. To ensure that each capillary tube 54 includes only one attached bead, an eyepiece 100 (see FIG. 5A) is provided for visually monitoring the capillary tubes 54 as they are lifted from the liquid. Although an eyepiece is illustrated, a variety of alternative mechanisms for confirming attachment of a single bead to capillary tubes 54 may be used, including laser and other optical detectors, cameras with pattern recognition, by pressure sensing internally within the capillary, and the like.

With a single bead attached to each capillary tube 54, platform member 38 is moved to align capillary tubes 54 with a desired row of test wells 78. Platform member 38 is then raised until the beads are placed into the target fluid of test wells 78. To release the beads, the vacuum is ceased to allow the beads to fall from capillary tubes 54. Optionally, a pressurized fluid, such as nitrogen, may be introduced into capillary manifold 36 through connector 58 to assist in expelling any of the beads from capillary tubes 54. The pressurized fluid will preferably remain on while removing capillary tubes 54 from the fluid to ensure that the beads will not re-adhere to the capillary tubes 54. The pressurized fluid will be provided from a pressure source (not shown) via suitable tubing (not shown) and will be monitored and regulated by a dispense pressure gauge 102 and a dispense pressure regulator 104. In alternative manual method, the beads may simply be physically touched off the capillary where they fall onto a surface.

After the beads have been dispensed into test wells 78, platform member 38 is moved to align capillary tubes 54 with wash wells 84 of miscellaneous plate 76. Platform member 38 is then raised to place capillary tubes 54 in wash wells 84 and a vacuum is created in capillary tubes 54 to draw the washing solution into capillary tubes 54. Pressure is then supplied to capillary tubes 54 to expel the washing solution from capillary tubes 54, and platform member 38 is moved to align capillary tubes 54 with the pools of beads in wells 80 or 82 as previously described. The wash pressure is continued to be applied as the capillary is removed from the wash solution to ensure that wash solution does not re-enter the capillaries. The process of attracting beads to capillary tubes 54 and distributing the beads to others of the test wells 78 is then repeated as previously described.

It will be appreciated that a variety of other embodiments for separating and then transferring beads are possible. For example, manual methods may comprise a wand having a pressure/vacuum source at one end and a capillary at the other end. The capillary may be placed into a well by grasping and manipulating the wand. A vacuum may then be applied to attach a bead to the capillary. After moving the bead from the well, pressure may be applied to release the bead. Other possible embodiments are illustrated in FIGS. 11–14.

Figure 11:
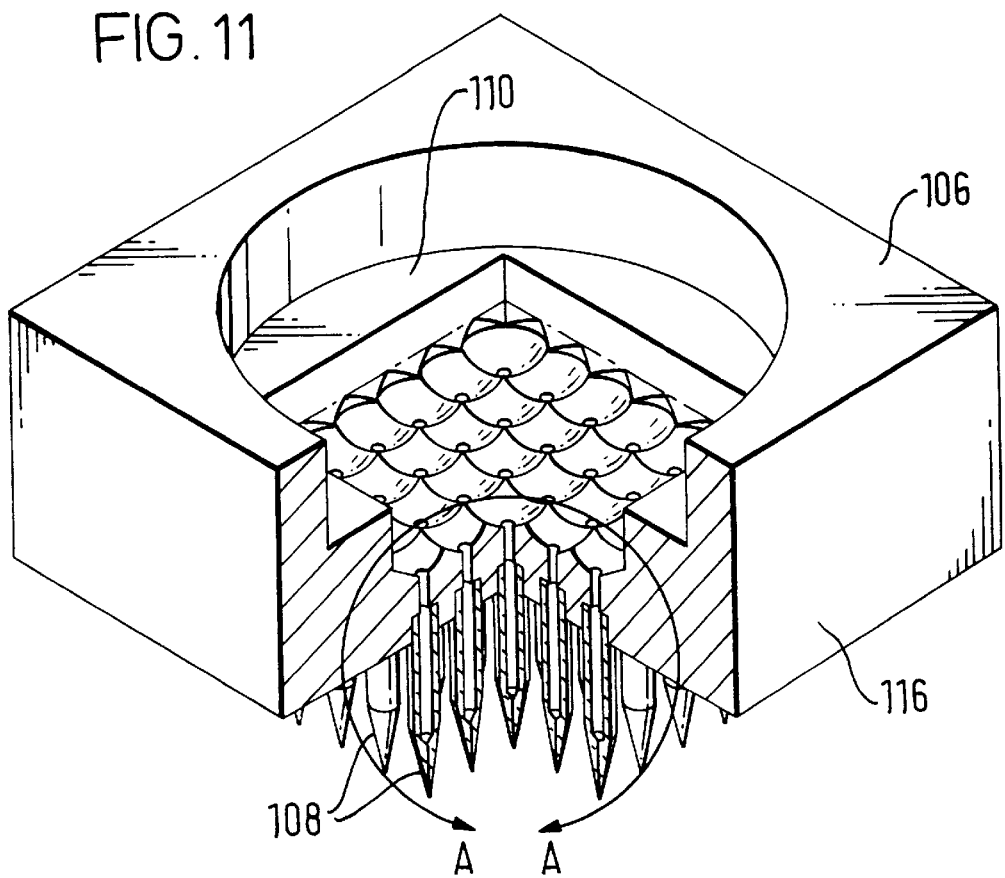
FIG. 11 is a cutaway perspective view of an alternative capillary manifold according to the present invention.
Figure 11A:
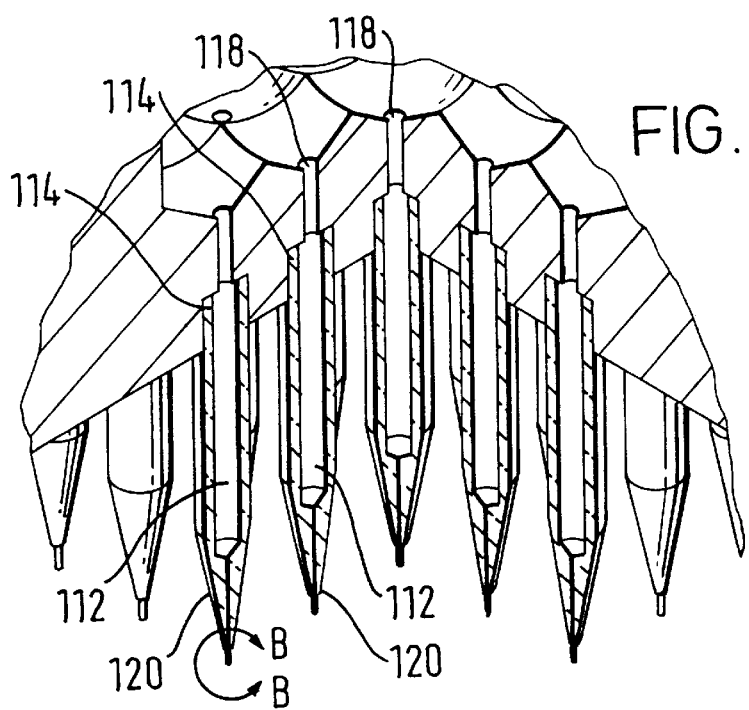
FIG. 11A is a more detailed view of FIG. 11 taken along lines A—A.
Figure 11B:
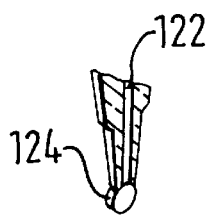
FIG. 11B is a more detailed view of a capillary tube of FIG. 11A taken along lines B—B.

Referring to FIGS. 11, 11A, and 11B, an alternative embodiment of a capillary manifold 106 will be described. Capillary manifold 106 includes an array of 36 capillaries 108 and is useful in distributing beads to an 864 well plate. Capillary manifold 106 may be substituted for capillary manifold 36 of system 30. Capillary manifold 106 includes an open interior 110 which is in communication with each of capillary tubes 108. In this manner, a vacuum or positive pressure may be created within open interior 110 to create a vacuum or pressure within capillary tubes 108. Capillary tubes 108 may be constructed to be essentially identical to capillary tubes 54 of system 30. As best shown in FIG. 11A, capillary tubes 108 include an elongate cylindrical lumen 112 at a proximal portion 114. Proximal portion 114 is inserted into a housing 116 having lumens 118 which extend into open interior 110. Capillary tubes 108 include a tapered distal portion 120 having a capillary 122 (see FIG. 11B). When a vacuum is created within capillary 122, a bead 124 is attracted to capillary tube 108 as shown in FIG. 11B. For beads having a mean size in the range from about 100 $\mu$m to about 200 $\mu$m, capillary 122 will preferably have a cross-sectional area in the range from about 40 $\mu$m to about 80 $\mu$m.

Figure 12:
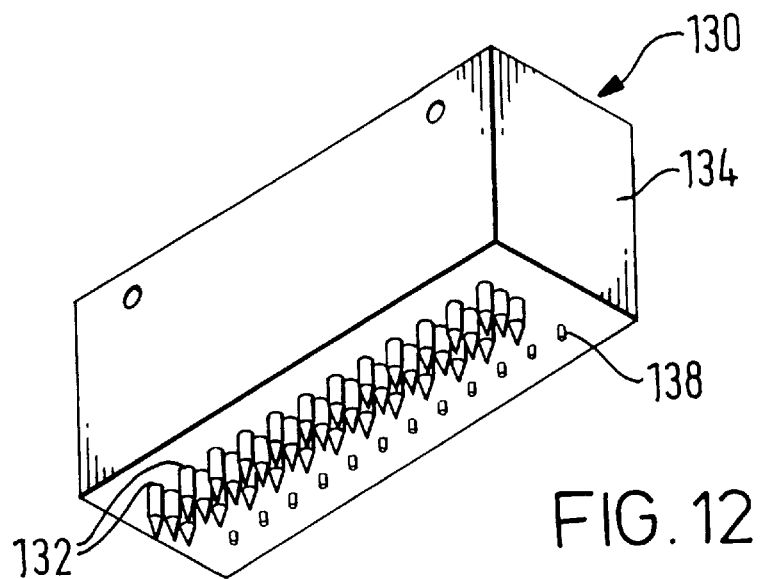
FIG. 12 is a perspective view of another alternative capillary manifold according to the present invention.
Figure 12A:
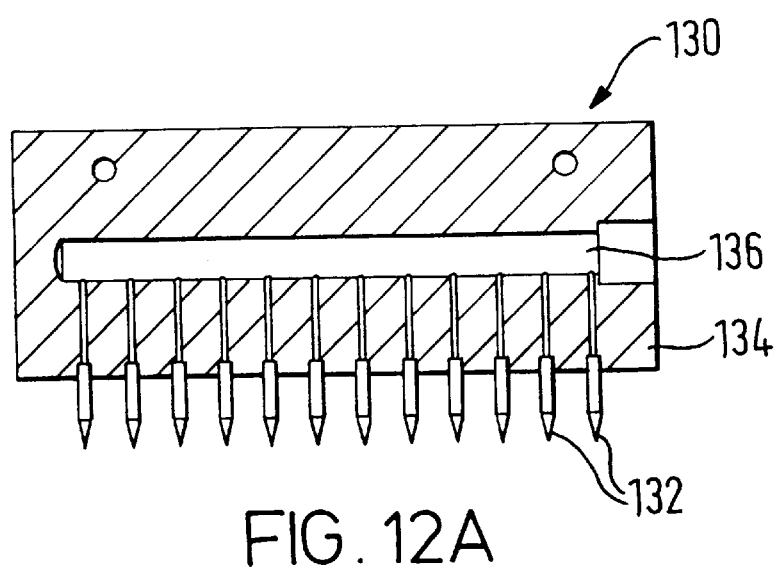
FIG. 12A is a cross-sectional side view of the manifold of FIG. 12.
Figure 12B:
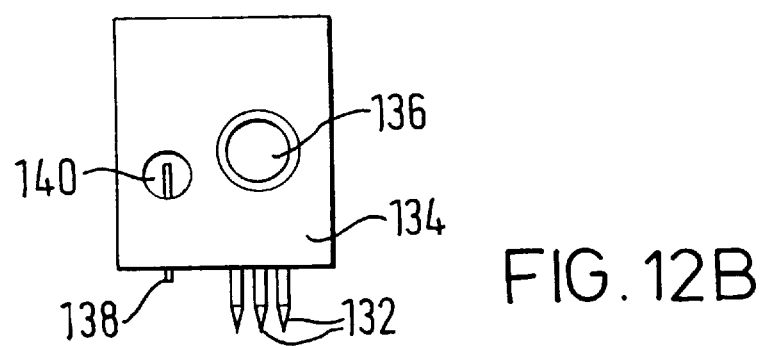
FIG. 12B is an end view of the manifold of FIG. 12.

Yet another embodiment of capillary manifold 130 is illustrated in FIGS. 12, 12A and 12B. Capillary manifold 130 includes thirty-six capillary tubes 132 which are directly inserted into a manifold body 134. A common lumen 136 is in communication with the capillary tubes 132 so that either vacuum or pressure may be supplied to tubes 132. Manifold 130 further includes target fluid delivery lines 138 similar to lines 64 of manifold 36. A lumen 140 is in communication with lines 138 to supply the appropriate fluid to lines 138. Hence, manifold 130 is similar to manifold 36 except that manifold 130 is provided with thirty-six capillary tubes for transferring thirty-six beads at a time.

Figure 13:
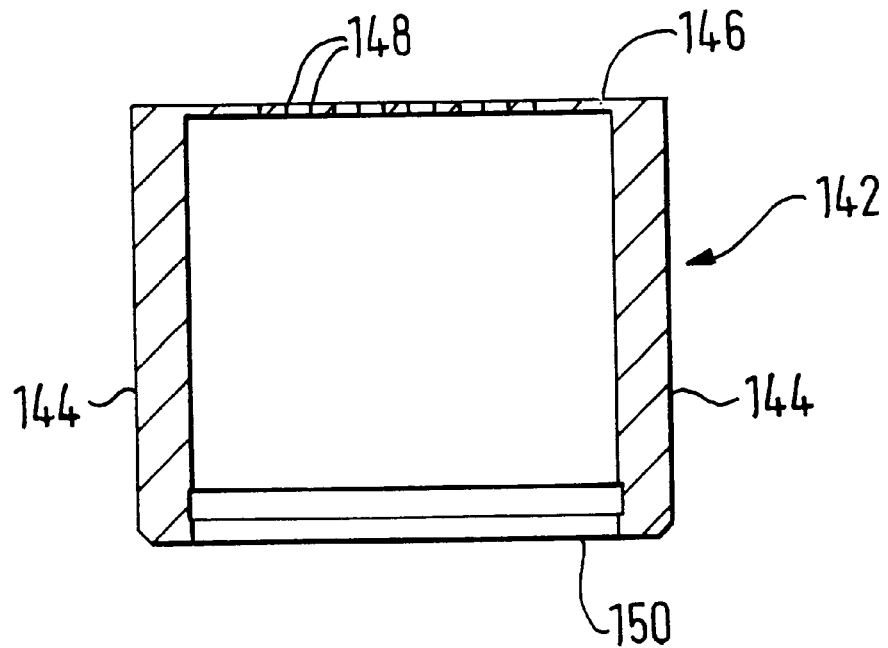
FIG. 13 is a cross-sectional side view of still yet another embodiment of a capillary manifold according to the present invention.
Figure 14:
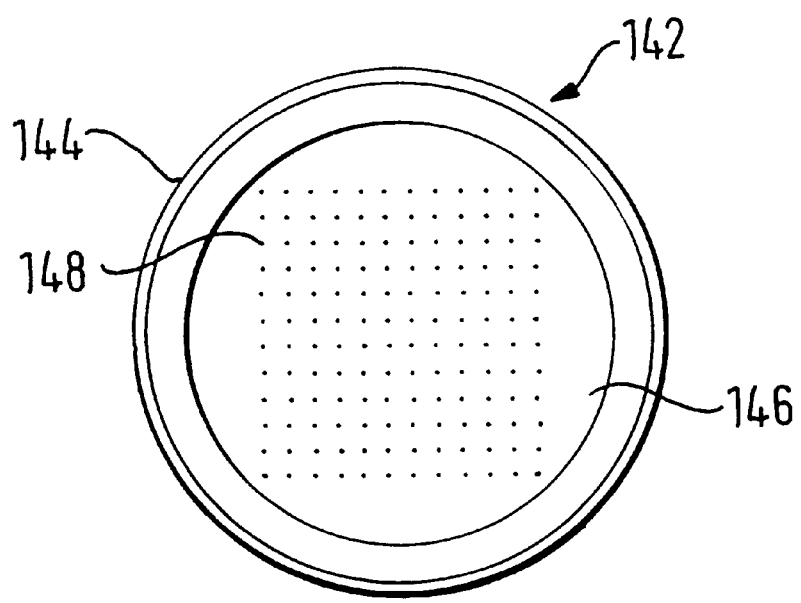
FIG. 14 is a bottom view of the capillary manifold of FIG. 13.

A further alternative manifold 142 is illustrated in FIGS. 13 and 14. Manifold 142 includes a body 144 having a generally flat face 146 which includes a plurality of small holes 148 in a closely-spaced array. Holes 148 are employed to each receive a single bead when face 146 is inserted into a well containing a plurality of beads held within a liquid. Holes 148 are preferably sized similar to the capillaries as described in previous embodiments. A vacuum is applied at an end 150 to draw the beads to holes 148 when face 146 is within the liquid. After the beads are attached, the manifold 142 is removed from the well and placed above a receiving target where pressure is applied at end 150 to remove the solid supports.

Figure 15:
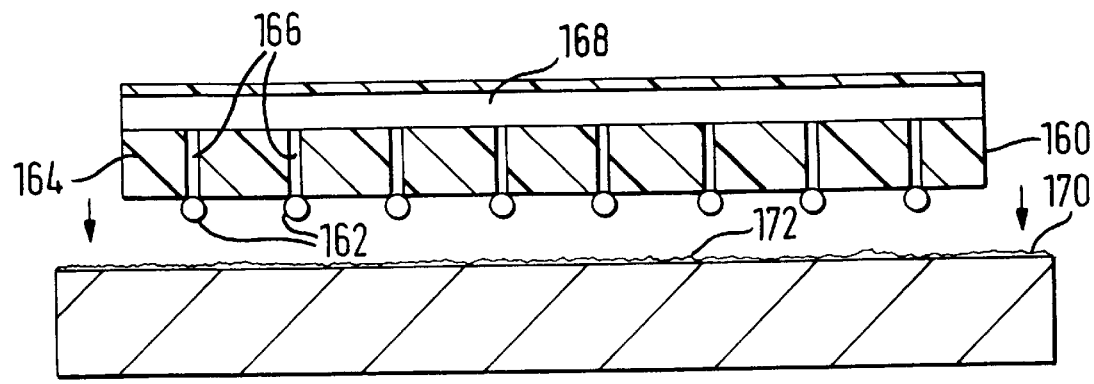
FIG. 15 is a cross-sectional side view of a disposable plate having a plurality of solid supports attached thereto. The plate is positioned above a surface having a reactive substance thereon according to the invention.

Referring now to FIG. 15, an exemplary plate 160 for processing a plurality of solid supports 162 will be described. As described below, one exemplary feature of plate 160 is that it may be constructed to be disposable so that it may be discarded after a single use, thereby eliminating the need to clean the plate after each use. Plate 160 comprises a housing 164 which includes a plurality of lumens 166 which are each in communication with a common lumen 168. A vacuum source (not shown) is preferably connected to common lumen 168 so that a vacuum may be drawn in each of lumens 166. In this manner, plate 160 may be positioned over a random group of solid supports and the vacuum supplied to attract a single solid support 162 to each of lumens 166. Lumens 166 will have a diameter that is smaller than the size of solid supports 162 so that the solid supports will engage housing 164 as shown. In this manner, the solid supports 162 are individualized and separated from each other when attracted to plate 160. By separating the solid supports, the compounds may be evaluated without contamination from each other. Although shown in an organized array, lumens 166 need not be fashioned in an organized pattern, although in some cases it may be desirable as described in greater detail hereinafter in connection with FIG. 16.

One particular advantage of plate 160 is that assays may be performed while the solid supports 162 remain attached. As shown in FIG. 15, assays may be performed by moving plate 160 into contact with a surface 170 having a reactive substance 172, such as bacteria, to allow the compounds on the solid supports to diffuse into substance 172. Short and limited diffusion times prevent cross-contamination of the released compounds.

By maintaining solid supports 162 attached to plate 160, the process of evaluating the compounds is made more efficient since the solid supports 162 do not need to be removed and transferred to another location to perform the assays. Following the release of the compounds, plate 160 may be discarded. This in turn eliminates the need for washing plate 160 after use to ensure that all of the lumens are clear. Instead, a new plate 160 may be used for each new set of solid supports. Furthermore, since clogging of the lumens is not a concern, the number of lumens that can be included in the plate may be increased. In this manner, the same amount of vacuum can be employed to attract larger numbers of solid supports to the plate.

Figure 16:
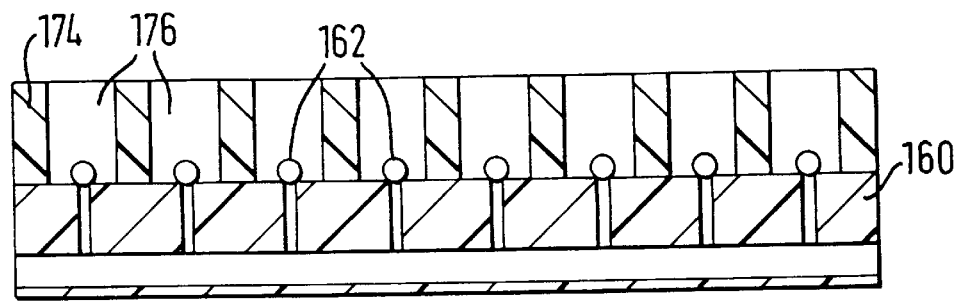
FIG. 16 illustrates the plate of FIG. 15 having a housing with a plurality of wells placed over the solid supports according to the invention.

As shown in FIG. 16, plate 160 may be coupled with other devices, such as a multi-well plate 174. Plate 174 includes a plurality of wells 176 which correspond in location to that of lumens 166 of plate 160. In this manner, each solid support 162 is isolated from each other so that assays can be performed on the compounds without cross-contamination. For example, reagents or other liquids may be introduced into each of wells 176 without contamination between the wells. As with the process described in FIG. 15, solid supports 162 may remain attached to plate 160 during evaluation of the compounds. In this manner, time is saved by not transferring the solid supports 162 to another device or location for evaluation. Use of multi-well plate 174 is further advantageous in that longer assays may be performed since the concern of cross-contamination is reduced.

Figure 17:
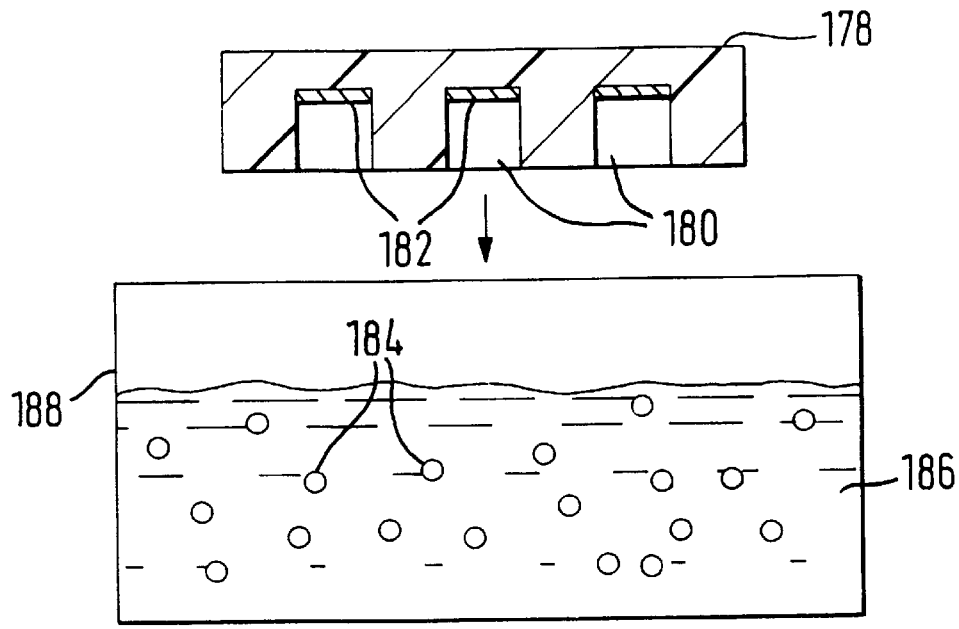
FIG. 17 is a cross-sectional view of an alternative plate having a plurality of wells with magnets included therein. The plate is positioned above a reservoir having solid supports, with a magnetic material being included on the solid supports according to the invention.

Referring to FIG. 17, an alternative embodiment of a plate 178 will be described. Plate 178 includes a plurality of wells 180 which each include a permanent magnet 182 to attract solid supports 184 into wells 180.

To attract solid supports 184 into wells 180, a magnetic material having a polarity that is opposite of magnets 182 is provided on each of the solid supports 184. This may be accomplished, for example, by including magnetic microbeads on or within each of the solid supports 184. The microbeads are several times smaller in magnitude than the solid supports, and the number of microbeads per solid support will depend upon the size of the solid support. Exemplary microbeads may comprise, for example, MACS Micro Beads.

As shown in FIG. 17, an exemplary method for attracting solid supports 184 into wells 180 is by suspending solid supports 184 in a liquid medium 186 that is held with a reservoir 188. Plate 178 is dipped into reservoir 188 and manipulated until each well 180 receives a single bead. The size of wells 180 is preferably configured such that only one bead will be able to fit within each well. Plate 178 is then removed from reservoir 188 so that evaluation of the compounds on the solid supports may proceed. One particular advantage of the magnetic microbeads is that they are removable from the solid supports so that they can be removed prior to performing assays on the compounds.

In one alternative, magnets 182 may be replaced with electrostatically charged regions which will attract solid supports 184 to the charged regions. In another alternative, magnets 182 may be replaced with a chemical treatment to allow covalent attachment of the solid supports to the wells. Alternatively, plate 178 may be constructed so that it does not include any wells but instead includes chemically treated areas which will allow attachment of solid supports 184 when placed into liquid medium 186. Exemplary chemical functionality that can be created on plate 178 include amines, carboxylic acids, or one member of a strong binding pair, such as biotin, streptaviloin, and the like.

In one alternative embodiment, the solid supports may be separated and organized on a surface having hydrophilic islands arrayed on a hydrophobic background. When a suspension of beads in water is placed onto the surface, the water and solid supports will tend to move to the hydrophilic islands, thereby segregating the solid supports onto individual islands.

Such a surface may be prepared using a silicon micromachined master to create the desired pattern. A replica of the silicon surface is then created with an elastomeric material and is employed as a stamp. This stamp is then placed onto the surface to provide the features of the stamp.

Figure 18:
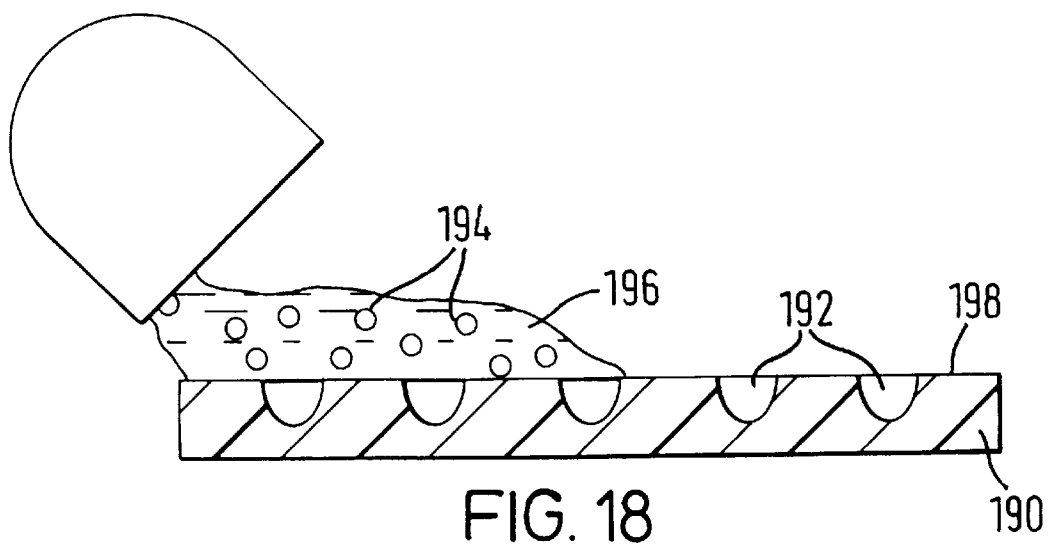
FIG. 18 illustrates yet another plate having wells therein, with a suspension of solid supports being placed thereon.
Figure 19:
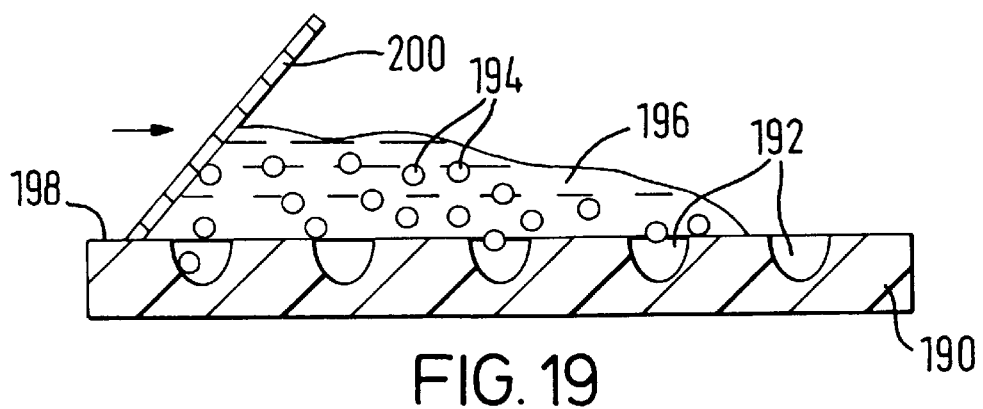
FIG. 19 illustrates the plate of FIG. 18 showing an edge being moved across the plate to move the solid supports into the wells according to the invention.

Referring to FIGS. 18 and 19, still yet another alternative plate 190 for receiving solid supports will be described. As shown in FIG. 18, plate 190 includes a plurality of wells 192 which are preferably sized to receive a single solid support or a known quantity of solid supports. A plurality of solid supports 194 are supplied to plate 190 by suspending solid supports 194 in a liquid medium 196 and pouring the suspension onto a top surface 198 of plate 190. Top surface 198 is preferably planar so that a straight edge 200 may be scraped across surface 198 as shown in FIG. 19 to move the solid supports 194 into wells 192 while removing any excess liquid medium 196 from the plate.

The liquid medium 196 will preferably comprise a molten agarose which will eventually solidify in wells 192. After the gel has solidified, scraping will preferably be repeated to further clean plate 190. Assays may then be performed to evaluate the chemicals on the solid supports.

Plate 190 will preferably be constructed from a plastic sheet having a high density array of wells machined therein. The concentration of solid supports 194 within medium 196 may be adjusted so that approximately one solid support will be provided for each well volume. An exemplary well volume is about one half a mL for solid supports having a size in the range from 100 $\mu$m to 200 $\mu$m.

Figure 20:
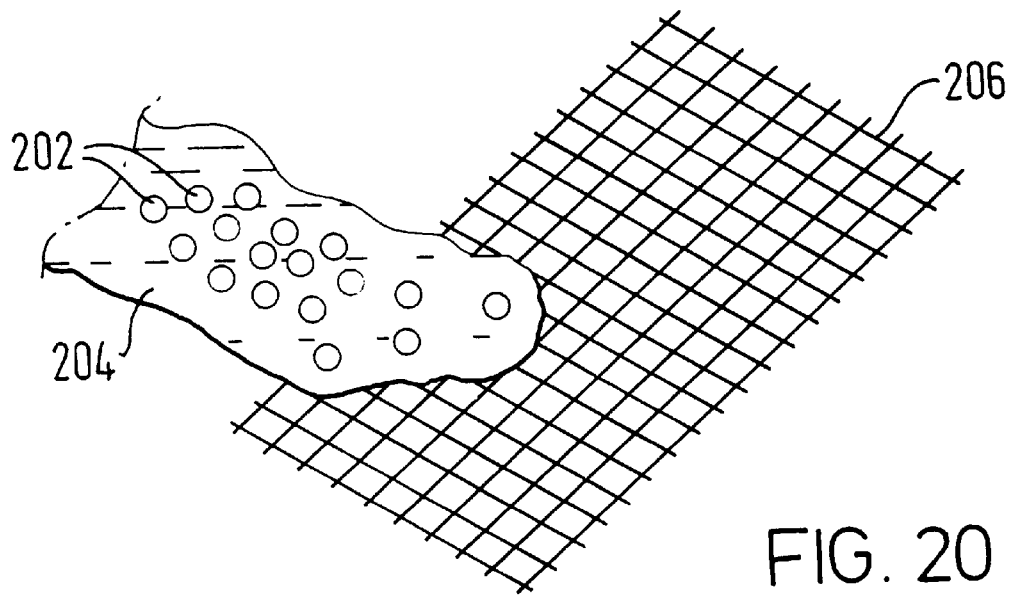
FIG. 20 illustrates a mesh material having a suspension of beads poured thereon according to the invention.
Figure 21:
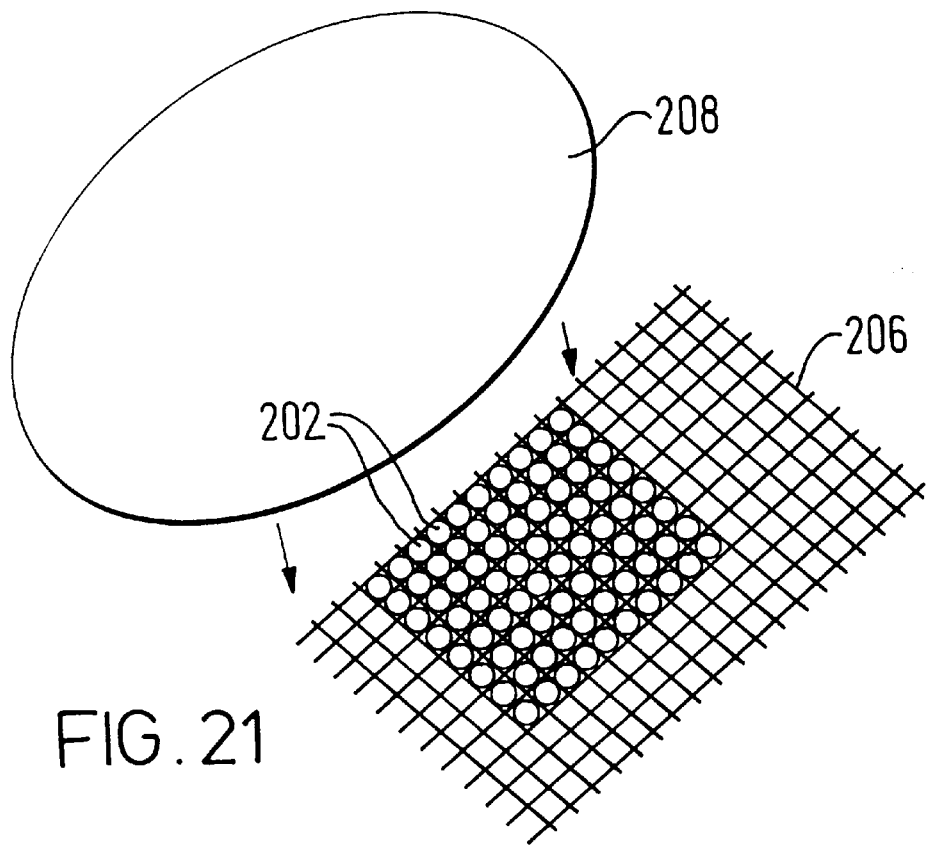
FIG. 21 illustrates the mesh material of FIG. 20 having the solid supports organized into an array and a plate which may be moved in contact with the solid supports to transfer the solid supports from the mesh material according to the invention.

FIGS. 20 and 21 illustrate another alternative way to organize and separate a plurality of solid supports 202 so that compounds on the solid supports may be evaluated. As shown in FIG. 20, solid supports 202 are included in a suspension material 204 which is poured onto a mesh material 206, such as a plastic mesh. Solid supports 202 are then manipulated until organized on the mesh material 206 as illustrated in FIG. 21. Optionally, a suction source may be provided below mesh material 206 to facilitate the organization of the solid supports 202.

Once organized in an array, a permeable surface 208 having an agarose gel thereon is placed against the solid supports 202 to transfer them to surface 208. Assays may then be performed on the solid supports while remaining attached to surface 208 or after being transferred to another location. Use of permeable surface 208 is advantageous in that cells may be grown thereon and a fresh media be placed below surface 208 to allow nutrients from the media to be supplied to the cells.

Figure 22:
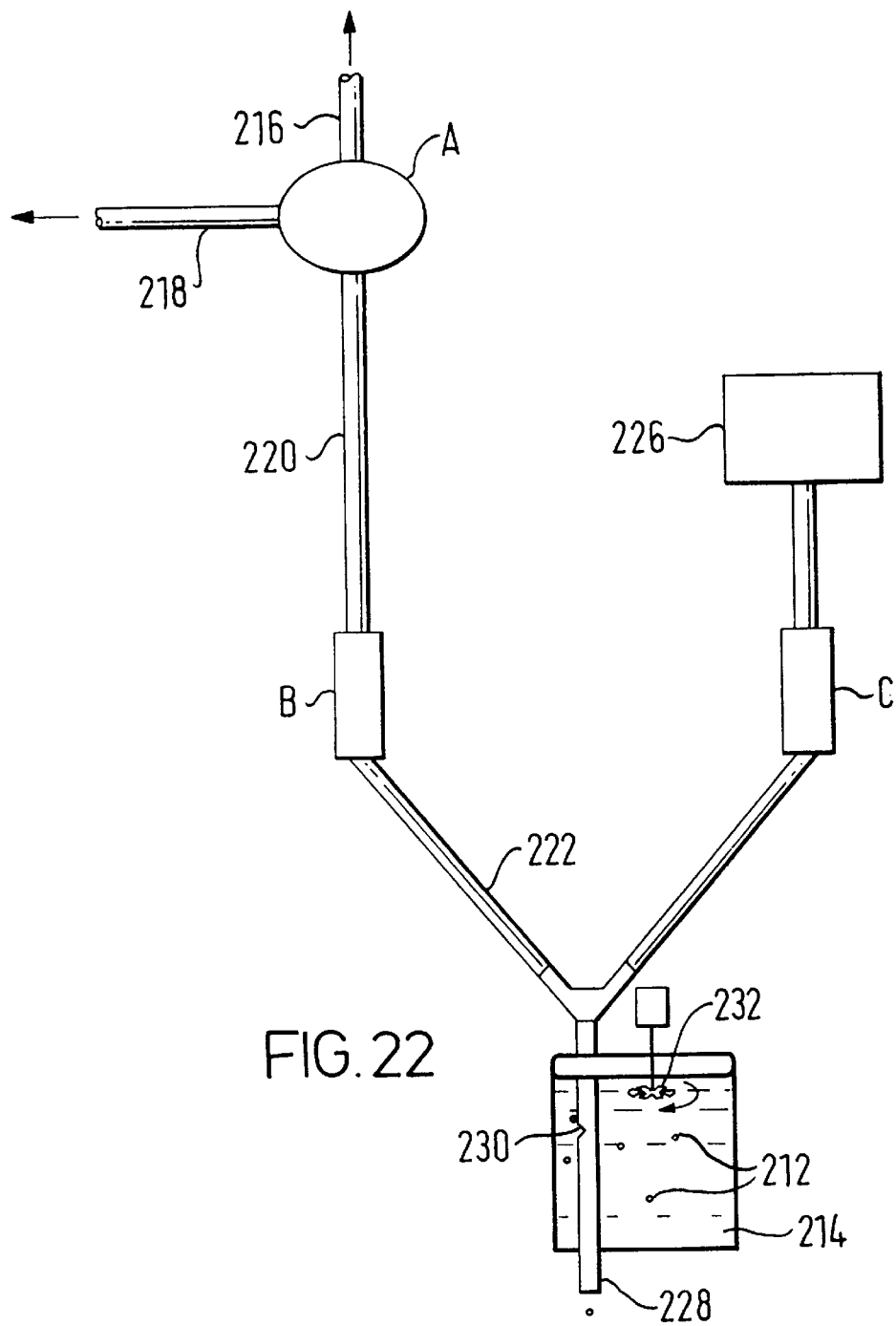
FIG. 22 illustrates a mechanism for swirling beads within a liquid medium so that the beads may be captured within a tube according to the invention.

FIG. 22 illustrates a system 210 for transferring solid supports 212 from a reservoir 214 to locations where the chemical compounds on the solid supports may be evaluated. System 210 comprises a three-way valve A, a pulse valve B and a pulse valve C. Connected to three-way valve A are three lengths of tubing 216, 218 and 220. Tubing 216 connects valve A to a pressure source while tubing 218 connects valve A to a vacuum source. Tubing 220 connects valve A to valve B. A length of tubing 224 connects valve C to a pressurized fluid reservoir 226. Extending between valve B and C is a length of tubing 222. Tubing 222 is fashioned in the shape of a V, with a length of tubing 228 extending from tubing 222 at the V connection. Tubing 228 includes a small hole 230 which is sized just large enough to receive a single solid support 212 within reservoir 214. An impeller 232 is held within reservoir 214 and may be rotated as shown to cause solid supports 212 to swirl within reservoir 214. The swirling action within reservoir 214 causes solid supports 212 to be captured within hole 230 so that the solid supports 212 may be dispensed from tubing 228 as shown.

Figure 23:
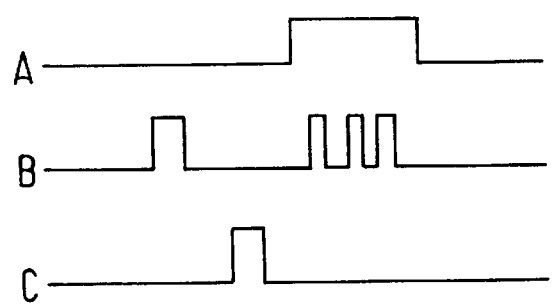
FIG. 23 is a timing diagram showing the operation of various pressure and vacuum sources of the mechanism of FIG. 22 according to the invention.

Operation of valves A, B and C is illustrated in FIG. 23. Valves A, B and C are normally closed, with lengths of tubing 218 and 220 being under a vacuum when valve A is closed. As solid supports 212 are swirled within reservoir 214, valve B is opened long enough to "draw" in a certain amount of liquid through hole 230 to capture a solid support 212 within tubing 228. Valve B is then closed and valve C is opened to introduce a small volume of liquid from reservoir 226 into tubing 228. This liquid is introduced to prevent the bead from sticking to the wall.

Valve C is then closed and valve A is opened to switch from vacuum to pressure. Valve B is then pulsed to introduce pressure into lengths of tubing 222 and 228 and to expel the captured solid support as shown.

Although system 210 is shown dispensing only a single solid support at a time, it will be appreciated that a number of such systems may be operated in parallel so that a plurality of solid supports may be transferred from a single or multiple reservoirs in parallel fashion to wells of a multi-well plate where evaluation of the chemical compounds may proceed.

Figure 24:
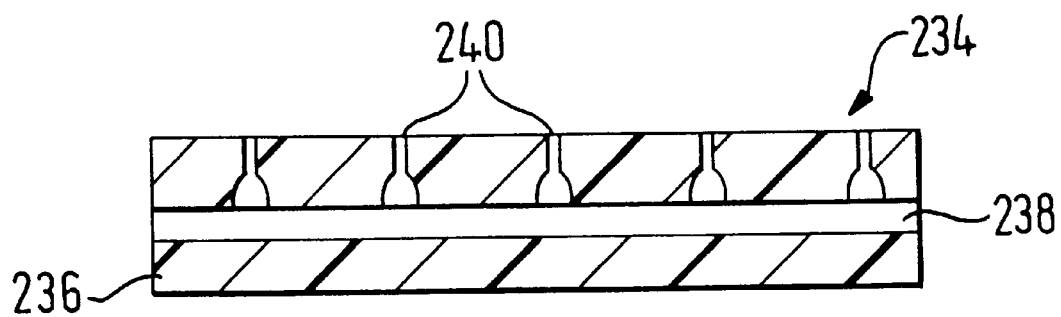
FIG. 24 is a cross-sectional side view of a housing having a central channel and a plurality of nodes for receiving solid supports according to the invention.
Figure 25:
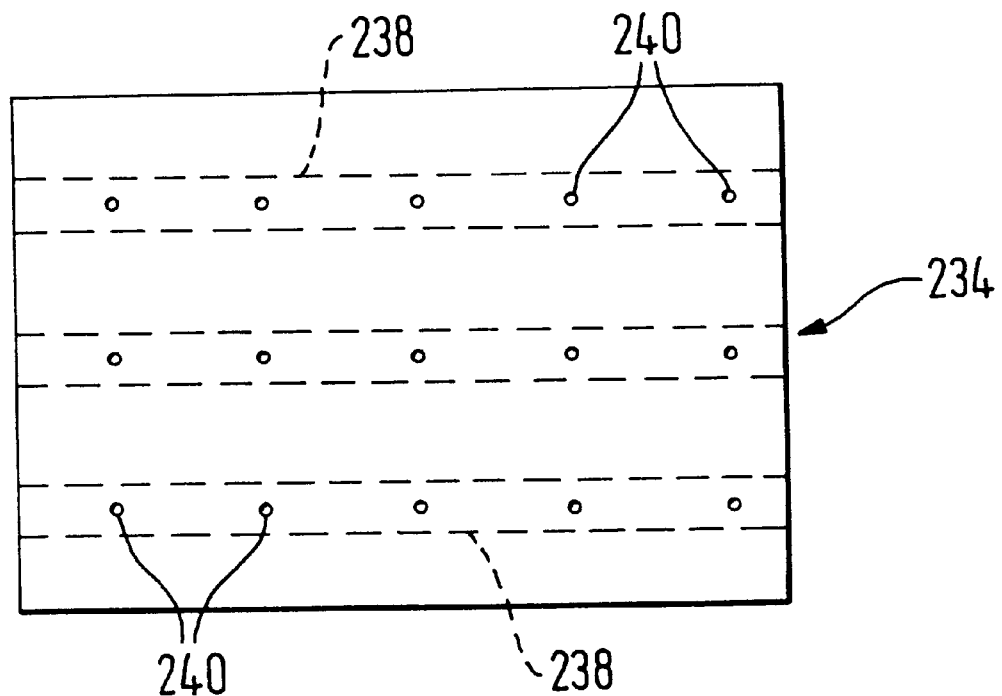
FIG. 25 is a top view of the housing of FIG. 24.

Referring now to FIGS. 24 and 25, an alternative system 234 for separating and organizing a plurality of solid supports will be described. System 234 comprises a housing 236 which includes a plurality of central channels 238 and a plurality of vented nodes 240 extending orthogonally from each of the channels 238. Microfabrication techniques may be employed to create channels 238 and nodes 240. System 234 operates by introducing a plurality of solid supports which are suspended in a suspension medium into each of the central channels 238. As the suspension is forced through channels 238, the suspension will move into nodes 240 by capillary forces. Optionally, a vacuum may be provided at each of the node vents to assist in drawing the solid supports into the nodes 240.

The suspension medium will continue to flow into nodes 240 the vents are until blocked by a solid support which will stop the flow. The flow of the suspension through channels 238 is continued until each of nodes 240 includes a solid support. In this manner, system 234 may be provided with multiple, e.g. thousands, of nodes so that large numbers of solid supports may be organized and separated from each other to facilitate evaluation of the chemical compounds.

One advantage of system 234 is that it may operate as a closed system. Such a system is advantageous in that small volumes of liquids can be employed because evaporation can be easily controlled.

Although the foregoing invention has been described in some detail by way of illustration and example, for purposes of clarity of understanding, it will be obvious that certain changes and modifications may be practiced within the scope of the appended claims.

What is claimed is:

1. A system for processing a plurality of beads, the system comprising:

a plurality of beads having a diameter in the range from about 5 $\mu$m to 300 $\mu$m;

a manifold comprising a housing having a plurality of spaced-apart and separated areas, wherein each area includes a capillary tube extending from the housing, and wherein the capillary tubes each have a distal end with an opening that is smaller than a single bead that is to be attracted to the distal end; and a vacuum source to create a vacuum within the manifold, wherein, upon application of the vacuum, at least a portion of the beads are attracted to the capillary tubes such that the attracted beads are separated and spaced-apart from each other while attracted to each capillary tube.

2. A system for processing a plurality of solid supports, the system comprising:

a plurality of beads having a diameter in the range from about 100 $\mu$m to 200 $\mu$m;

a manifold comprising a housing having a plurality of spaced-apart and separated areas, wherein each area includes a capillary tube extending from the housing, and wherein the capillary tubes each have a distal end with an opening having a diameter in the range from about 40 $\mu$m to about 80 $\mu$m; and a vacuum source to create a vacuum within the manifold, wherein, upon application of the vacuum, at least a portion of the beads are attracted to the capillary tubes such that the attracted beads are separated and spaced-apart from each other while attracted to each capillary tube.

3. The system of claim 1 or 2, wherein the vacuum is fluidly communicated through a lumen to the manifold.

4. The system of claim 1 or 2, wherein the areas are arranged in an organized pattern.

5. The system of claim 4, wherein the organized pattern is a two-dimensional array.

6. The system of claim 1 or 2, further comprising a common storage location for holding the beads prior to the application of the vacuum and the attraction of the beads to the areas.

* * * * *